United States Patent [19]

Freeman et al.

[11] Patent Number: 4,904,592
[45] Date of Patent: Feb. 27, 1990

[54] STABILIZED ENZYMES

[75] Inventors: Amihay Freeman, Ben Shemen; Ruth Tor, Kiryat Ono, both of Israel

[73] Assignee: Ramot University For Applied Research & Industrial Development Ltd., Israel

[21] Appl. No.: 219,927

[22] Filed: Jul. 15, 1988

[30] Foreign Application Priority Data

Aug. 6, 1987 [IL] Israel .......................................... 83451

[51] Int. Cl.$^4$ ................................................ C12N 9/00
[52] U.S. Cl. ..................................... 435/183; 435/182
[58] Field of Search ................................. 435/182, 183

[56] References Cited

U.S. PATENT DOCUMENTS

| 4,390,632 | 6/1983 | Carter | 435/183 |
| 4,434,228 | 2/1984 | Swann | 435/182 |
| 4,436,813 | 3/1984 | Wood | 435/182 |
| 4,464,468 | 8/1984 | Avrameas | 435/182 |

Primary Examiner—Peter D. Rosenberg
Attorney, Agent, or Firm—Steinberg & Raskin

[57] ABSTRACT

Enzymes are stabilized by encagement in a double layer having a polyaldehyde base coat linked to the amino groups of the enzyme, and an outer polymer coat cross-linked therewith. The outer coat is made of a polymer which in the unlinked state has free amino and/or acyl hydrazide groups.

Optionally the stabilized enzyme is immobilized within a matrix.

Processes for the preparation of the encaged and optionally immobilized enzymes are described.

16 Claims, 3 Drawing Sheets

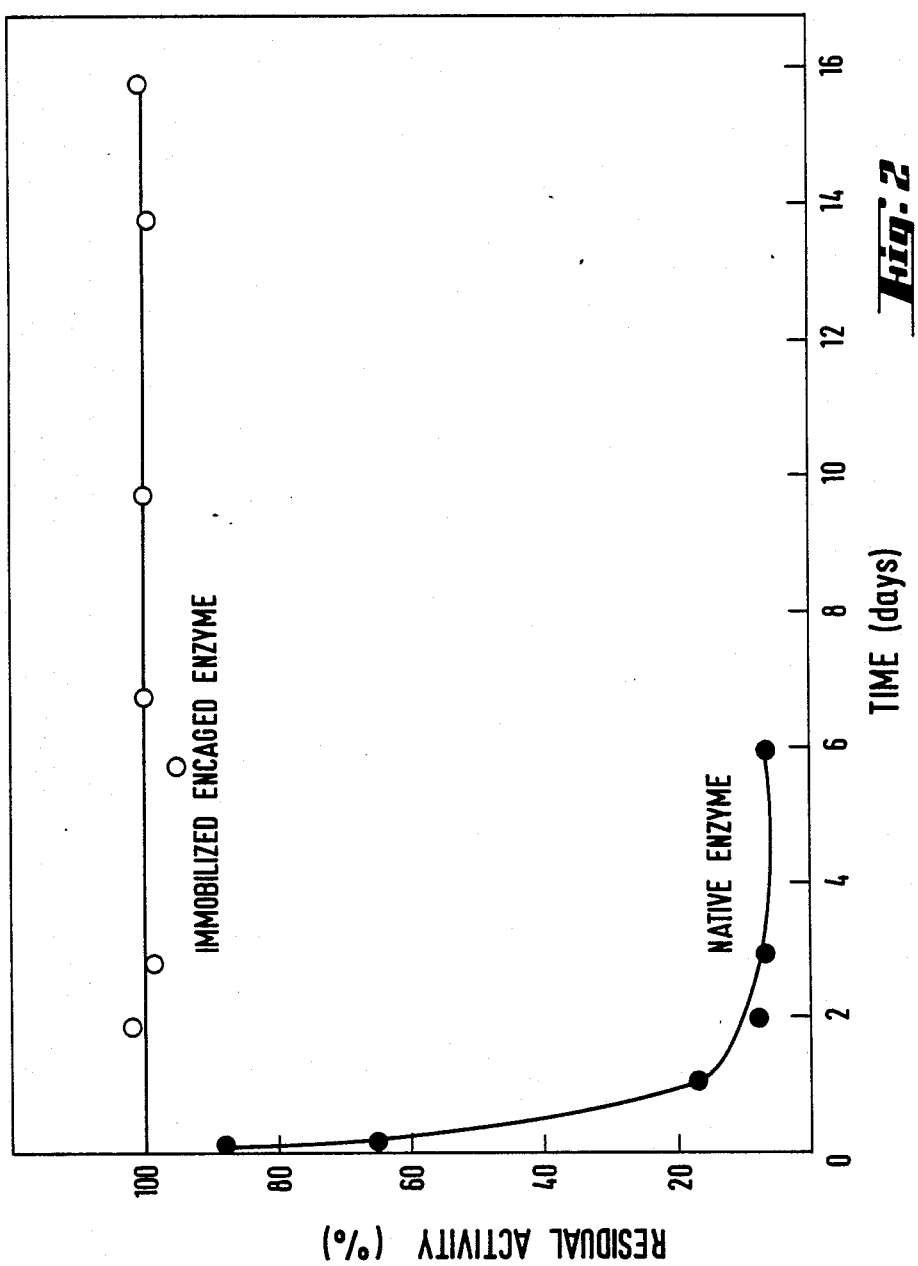

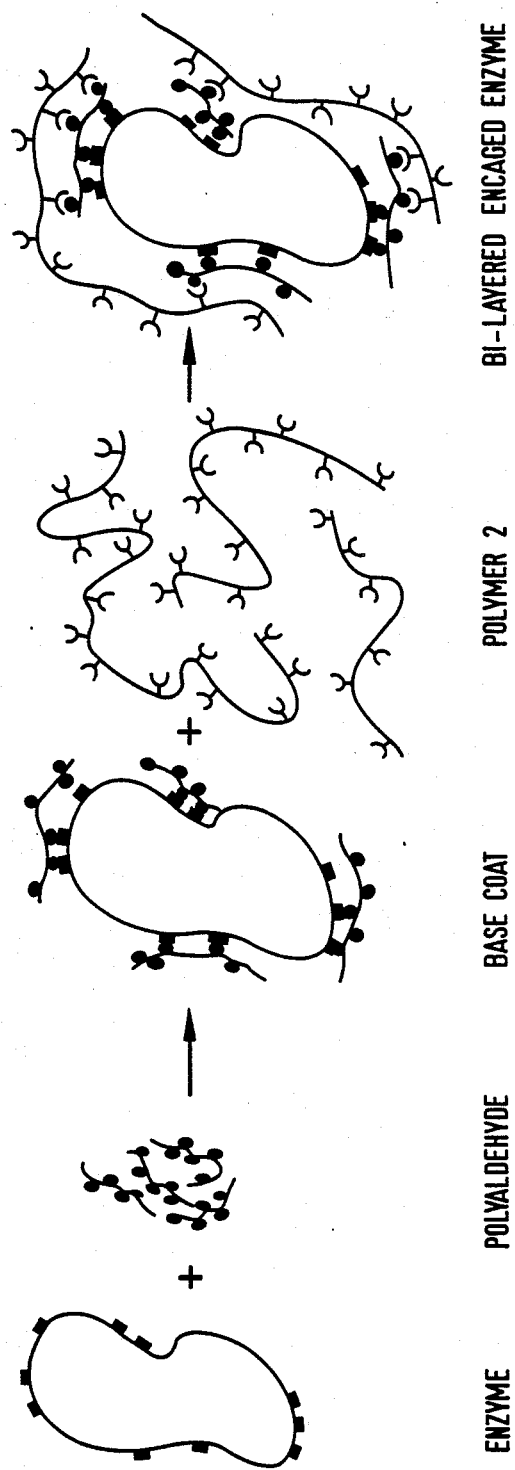

STABILIZED ENZYMES

BACKGROUND OF THE INVENTION

The invention concerns a stabilized enzyme product and a method for its preparation. The stabilized enzyme product may be in form of an aqueous solution or a lyophilized dry product. A stabilized enzyme product according to the invention may optionally be further stabilized by immobilization.

LIST OF REFERENCES

1. Klibanov, A. M., *Adv. Appl. Microb.* 1983, 29, 1–28.
2. Martinek, K. and Berezin, I. V., *J. Solid Phase Biochem.* 1978, 2, 343–385.
3. Butler, L. G., *Enzyme Microb. Technol.*, 1979, 1, 253–259.
4. Martinek, K., Klibanov, A. M., Goldmacher, V. S. and Berezin, I. V., *Biochim. Biophys. Acta* 1977, 485, 1–12.
5. Klibanov, A. M., *Anal. Biochem.* 1979, 93, 1–25.
6. Schmid, R. D. *Adv. Biochem. Eng.* 1979, 12, 41–118.
7. Back, J. R., Oakenfull, D. and Smith, M. B., *Biochemistry* 1979, 18, 5191–5196.
8. Tonchilin, V. P. and Martinek, K., *Enzyme Microb. Technol.* 1979, 1, 74–82.
9. Greco, G. and Gianfreda, L., *Biotechnol. Bioeng.* 1981, 23, 2199–2210.
10. Wykes, J. R., Dunill, P. and Lilly, M. D., *Biochim. Biophys. Acta* 1971, 250, 522–529.
11. Marshall, J. J., *Trends in Biochem. Sci.* 1978, 3, 79–83.
12. Lenders, J. P. and Crichton, R. R., *Biotech. Bioeng.* 1984, 26, 1343–1351.
13. Hixon, H. F., *Biotech. Bioeng.* 1973, 15, 1011–1016.
14. Von Specht, B. U., Seinfeld, H. and Brendel, W., *Hoppe-Seyler's Z. Physiol. Chem.* 1973, 354(s), 1659–1660.
15. Paz, M. A., Blumenfeld, O. O., Rojkind, M., Henson, E., Furfine, C., and Gallop, P. M., *Arch. Biochem Biophys.*, 1965, 109, 548–559.
16. Gary, W. L., Johnson, R. N. and Kho, B. T., *J. Chromatog.* 1978, 156, 285–291.
17. Freeman, A., *Methods. Enzymol.* 1987, 135, 216–222.
18. Collinson, E., Dainton, F. S. and McNaughton, G. S., *Trans. Faraday Soc.* 1957, 53, 489–498.
19. Freeman, A. and Aharonowitz, Y., *Biotech. Bioeng.*, 1981, 23, 2747–2759.
20. Reuveny, S., Mizrahi, A., Kotler, M. and Freeman, A., *Biotech. Bioeng.* 1983, 25, 469–480.
21. Blank-Koblenc, T., Tor, R and Freeman, A., *Biotechnol. Appl. Biochem.*, 1988, 10, 32–41.
22. Nichols, C. S. and Cromartie, T. H., *J. Chem. Educ.*, 1979, 56, 832–834.
23. Samuni, A., *Anal. Biochem.*, 1975, 63, 17–26.
24. Malikkides, C. O. and Weiland, R. H., *Biotech. Bioeng.* 1982, 24, 1911–1914.
25. Freeman, A., Blank, T. and Haimovich, B., *Annal. N. Y. Acad. Sci.*, 1983, 413, 557–559.
26. Goldstein, L. and Manecke, G., *Appl. Biochem. Bioeng.*, 1976, 1, 23–126.
27. Dror, Y., Cohen, O. and Freeman, A., *Enz. Microb. Technol.*, 1988, 10, 273–279.

BACKGROUND OF THE INVENTION AND PRIOR ART

One of the intrinsic problems often hindering further development of analytical and synthetic applications of enzymes is the inherent instability of many enzymes. This limitation is crucial in particular in the case of applications involving prolonged exposure of the enzyme to elevated temperatures or to the presence of organic solvents (refs. 1, 2, 3).

Loss of enzymic activities may result from several factors imposing their effect via different mechanisms, of which the structural unfolding of the enzyme is the most abundant (refs. 2,4).

Enzyme stabilization by means of restrictions imposed on the enzyme, limiting its large conformational changes, was in the past attempted by either of two main approaches: rigidification of protein structure by multi-point attachment to water insoluble polymeric supports (refs. 1, 2, 4, 5), or by the addition of various solutes (refs. 6, 7, 8,9).

Several reports in literature describe coupling of water soluble polymers to enzymes, aiming towards the stabilization of enzymes in soluble form (for review see ref. 1). Thus, water soluble enzyme-polymer conjugates, prepared by enzyme coupling to polysaccharides (refs. 1, 10, 11, 12), polyvinylalchohol (ref. 13), polyvinylpyrrolidone (ref. 14) and polymethacrylic acid (ref. 4) were described.

Effective stabilization of soluble enzymes via this approach strongly depends on obtaining an intensive multipoint polymer - enzyme interaction, in a complementary way (ref. 1,4). The effectiveness of such enzyme - polymer conjugates will also depend on the chemical nature of the polymeric moiety, creating a hydrophilic or charged microenvironment in the immediate surrounding of the enzyme. The most effective conjugate of this kind seems to be the chymotrypsin-polymethacrylic acid conjugate, prepared by the copolymerization of methacrylic acid and acryloyl chloride treated enzyme (ref. 4). The resulting poly - anionic enzyme derivative exhibited stability comparable to that of the gel entrapped enzyme analogue, prepared by copolymerization of methacrylamide or acrylamide, with bisacrylamide and acryloyl chloride treated enzyme.

SUMMARY OF THE INVENTION

In accordance with the invention there is provided a stabilized, biologically active water soluble enzyme product, characterized by enzyme molecules having a bi-layer protective structure comprising a polyaldehyde base coat linked to free amino groups of the enzyme, and cross-linked therewith an outer polymer coat, the polymers constituting said outer coat being of a kind which in the unlinked state comprises free amino and-/or acyl hydrazide groups.

The invention further provides a method of making a stabilized, biologically active enzyme product of the kind specified, characterized in that in a first step a native enzyme product is reacted in aqueous solution with an excess of a water-soluble polyaldehyde to produce an intermediary enzyme product in which the enzyme molecules are coated with said polyaldehyde base coat, and in a second step said intermediary enzyme product is reacted in aqueous solution with a polymeric reagent bearing free amino and/or free acyl hydrazide groups.

The bi-layer protective structure provided in accordance with the invention will occasionally be referred to hereinafter as "cage" and its production as "encagement". It provides several advantages over the prior act, such as:

The "cage" concept is of a general nature and enables also the stabilization of enzymes bearing low numbers of lysil residues. This is so because the polyaldehyde used in the first step amplifies the total number of cross-linking bridges formed and consequently, as distinct from the prior art (ref. 4) the stabilization degree will not depend solely on the lysil content of the enzyme (ref. 4).

The encagement method is based on the use of water soluble polymeric reagents, and is thus virtually free of toxic and inhibitory effects which occur when low molecular weight reagents have to be used such as, for example, acryloyl chloride, and acrylamide.

The "cage" concept allows for control of the microenvironment of the "encaged" enzyme by suitably modifying or selecting the chemical nature of the polymeric reagent used in the formation of the outer coat. For example, hydrophilicity or hydrophobicity may be introduced into the said polymeric reagent as may be required by the nature of the enzyme or its intended use.

Due to the combined effect of the two constituent "cage" coats, the stabilization of the enzyme is more effective as compared to single coat enzyme-polymer conjugates.

The nature of the reactants in said first and second steps is not critical. Thus, in the first step any water soluble polyaldehyde may be used that is capable of reacting with free amino groups forming part of lysil residues of the enzyme, a typical example being polyglutaraldehyde. Likewise there is no criticality in the selection of the water soluble polymeric reagent used in the second step, provided it bears free amino and/or acyl hydrazide groups, since it is these groups that cross-link with carbonyl groups of the polyaldehyde base coat. Typical examples of polymeric reactants used in the second stage are polyacrylamides, N-alkylated polyacrylamides, acylhydrazide or amino derivatives of polyacrylamides, polyvinylhydrazides, polyvinylamines, polylysine, various proteins and the like.

If desired, a stabilized enzyme product with "encaged" enzyme molecules according to the invention may be further stabilized by immobilization. As the outer coat of the stabilized enzyme according to the invention is made of polyacrylamide-amine or acyl hydrazide derivatives, its immobilization, either by chemical binding or crosslinking, is readily available. The latter method is particularly suitable seeing that the stabilized enzyme solution obtained at the end of the second step containes a large excess of unbound polymer which may be employed to form a matrix by appropriate crosslinking. Immobilization of enzymes by means of gel matrices is known per se and was successfully employed for the immobilization of enzymes in gels made of polyacrylamide-hydrazide crosslinked by glyoxal (refs. 21, 25).

It is believed that the stabilization of "encaged" enzymes according to the invention results from a combination of two effects. For one there occurs physical suppression of the unfolding process by the crosslinked polymeric "cage" built around the enzyme. Secondly there occurs a chemical suppression of conformational changes due to the microenvironmental effect of the bound hydrophylic polymeric moiety.

A stabilyzed enzyme product according to the invention may be stored in aqueous solution or be lyophilized into dry powder and stored as such. It has surprisingly been found in accordance with the invention that lyophilization of the "encaged" enzyme product according to the invention further increases its stability. Furthermore, immobilization of lyophilized "encaged" enzyme in glyoxal crosslinked polyacrylamide-hydrazide gel results in maximal amplification of this stabilization approach.

The stabilized and optionally immobilized enzyme products according to this invention may be used in a variety of enzyme catalyzed chemical processes, whether carried out batchwise or continuously.

BRIEF DESCRIPTION OF THE DRAWINGS

For better understanding the invention will now be described with reference to the annexed drawings, in which:

FIG. 2 is a diagram showing the thermal stability of a lyophilized "encaged" pig liver esterase entrapped in a polyacrylamide-hydrazide gel in accordance with the invention, in comparison to the behaviour of native pig liver esterase under similar conditions; and FIG. 3 is a schematic illustration of the formation a bi-layer protective cage in accordance with the invention.

DESCRIPTION OF THE PREFERRED EMBODIMENTS

Figure 1:
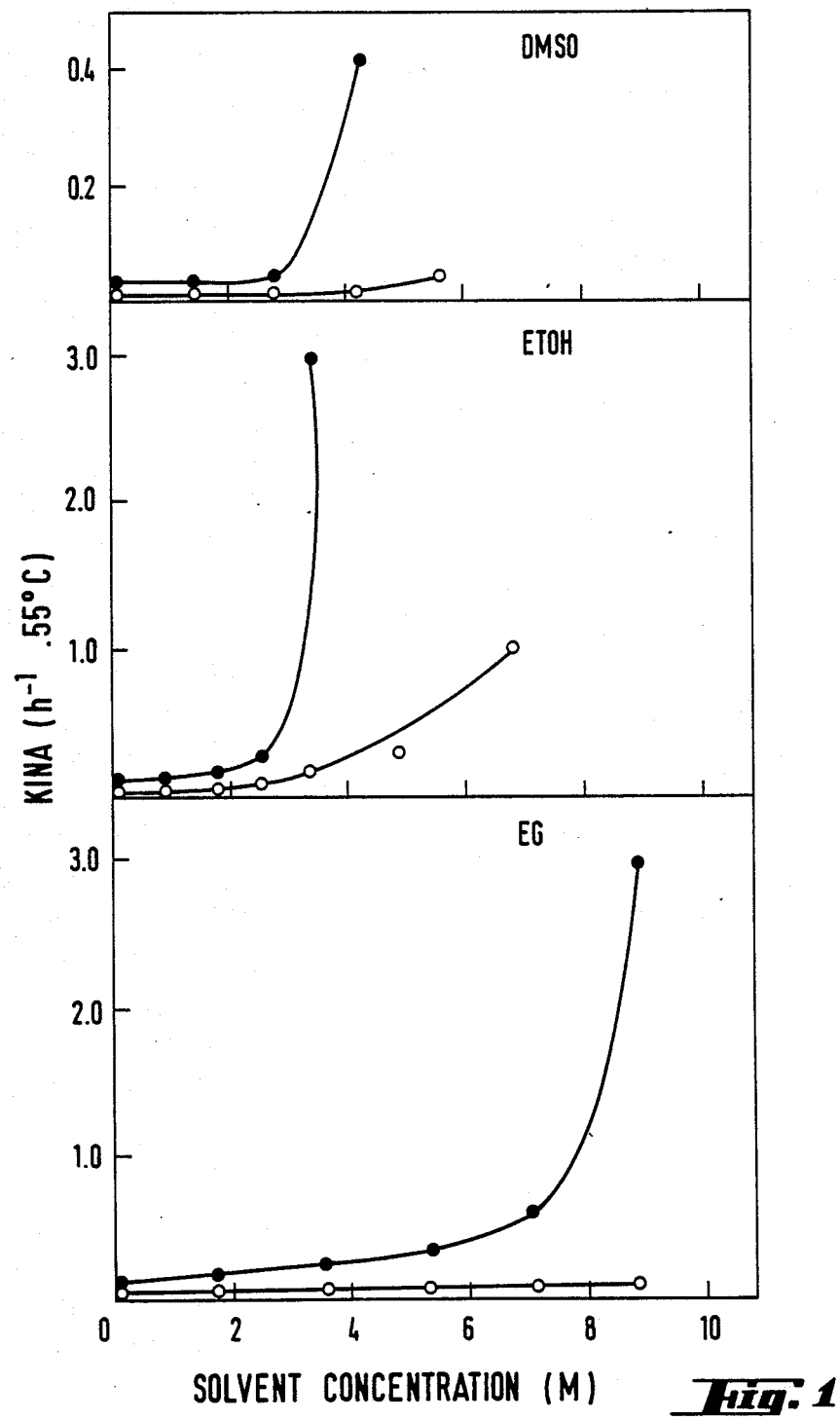
FIG. 1 is a diagram showing the stabilization of pig liver esterase by "encagement" in accordance with the invention expressed by resistance to combined temperature -cosolvent denaturation effects by three different solvents, in comparison to the behaviour of native carboxylesterase under similar conditions.

The stabilization of "encaged" enzymes according to the invention in aqueous solution and in the presence of water miscible organic solvents was investigated. Stabilization against denaturation by organic co-solvents is of great practical value as such cosolvents may be employed for the enhancement of substrate and product solubilities and the reversal of "natural" reaction routes (refs. 3,21). The stabilization effect was estimated by measuring inactivation-rate constant (Kina) values for native and "encaged" enzymes (lyophilized) incubated at 55° C. in the presence of cosolvent. Cosolvents, representing the group exhibiting only mild interference with the retention of enzyme stability in their presence (e.g. ethylene glycol, DMSO (ref. 21)), as well as cosolvents exhibiting strong denaturating effect (e.g. ethanol) were employed and the stabilization according to the invention was found to be effective with solvents of both groups. In FIG. 1, the empty circles stand for a stabilized encaged carboxylesterase according to the invention and the blackened circles stand for the native enzyme, and it is clearly seen that the rate of inactivation of the former is much lower than of the latter. This enhanced stability against denaturation by ethylene glycol, DMSO and ethanol allows for a significant increase in the content of the cosolvent present, without impairing the enzymic activity. Stabilized enzyme products according to the invention can thus be used to advantage as catalysts in the performance of reactions in which co-solvents are required from the outset or form in the course of the reaction.

FIG. 2 shows that a lyophilized "encaged" and immobilized enzyme product according to this invention (empty circles) retained its activity over sixteen days virtually without any change, while that of a native enzyme (blackened circles) dropped sharply during day 1 and from then on approached asymptotically zero activity. In these tests the enzymes were incubated at 55° C. in 0.05M Tris buffer (pH 8) and the activities were periodically tested.

FIG. 3 illustrates schematically the formation of a bi-layer "encagement" in accordance with the invention. As shown, in a first step an enzyme molecule is reacted with a polyaldehyde to yield an enzyme with a base coat. This product is then reacted with a "Polymer 2" being an amino and/or acyl hydrazide groups bearing water soluble polymer, to yield an enzyme within a bi-layered cage in accordance with the invention.

The invention will now be further described in the following examples to which it is not limited. All temperature indications are in centigrades.

EXAMPLE 1

Stabilization of Glucose Oxidase (E.C.1.1.3.4) by Bilayer Encagement

1. Preparation of polymeric reagents:

(a) Water soluble polymeric glutardialdehyde:

Into a 100 ml round bottomed flask, thermostated at 50° C., 20 ml of 1M $K_2CO_3$ (pH=10) were added, followed by 20 ml of 25% (w/v) glutardialdehyde (Merck, Cat. No. 4239). The polymerization reaction was allowed to proceed at 50° C. for 2 h. The reaction mixture was then cooled to room temperature, the pH brought to 7 by the addition of concentrated HCl and precipitates removed by centrifugation (7000 rpm for 10 min.). The remaining solution was then added into a ten fold volume of acetone to remove $K_2CO_3$ and salts by precipitation. The solution was then separated, the acetone evaporated and the remaining solution lyophilized and stored at −20° C. (yield: 3.3 g; 66%).

The water soluble polymeric glutardialdehyde thus obtained contained 0.35 mmole aldehyde groups per g (dry weight) determined according to J. S. Thompson and G. D. Shockman (1968) (Analytical Biochemistry 22, 260–268) and its MW estimated from gel filtration ("Biogel" p-6) against protein standards to be 1000.

(b) Preparation of Polyacrylamides:

b-(1) Polyacrylamide of MW=8000:

Into a one liter round bottomed flask, equipped with a magnetic stirrer, 680 ml of water were added. The temperature was brought to 4° C. by means of an ice bath and, under nigrogen flushing, 4 g (0.056 mole) of acrylamide monomer were added. Following complete monomer dissolution, 4.6 ml (0.034 mole) of N,N,N,N-tetramethylethylenediamine were added, followed immediately by 20 ml of 0.8777M (4 g in 20 ml) ammoniumpersulfate. The polymerization reaction (over ice, under nitrogen atmosphere) was allowed to proceed for one hour.

The polymer solution was then added dropwide into 3.5 l ice cold methanol, the precipitate separated by filtration, stored overnight at 4° C. under methanol, separated and dried on a rotavapour for 30 min at 40° C. The polymer was finally dried by dessication in vacuo over $P_2O_5$. The dry polymer was stored in a tightly closed vessel at room temperature (yield 3.2 g (80%)).

b-(2) Alkylamine - derivative:

Into a 0.25 l round bottomed flask equiped with a magnetic stirrer 100 ml ethyleneglycol were added and the temperature adjusted to 50° C. (oil bath). One g of polyacrylamide was added and dissolution was allowed to proceed at 50° overnight. The temperature was then adjusted to 100° C. and 13 ml (0.13 mole) 1,4 diaminobutane were added. The aminolysis reaction was allowed to proceed at 100° C. for 3 hrs. The solution was then cooled over ice and mixed with 100 ml of ice cold 2N HCl. The pH of this solution was adjusted to 6.3 and the solution dialyzed (four times: against 5 liters of 0.02M phosphate, pH 6.3; 0.02M phosphate, pH 6.3; 0.02M phosphate, pH 6.3; and finally water). The polymer was finally recovered by lyophilization (yield: essentially quantitative, amine content 2 meq/g dry polymer (12.5% conversion, determined titrimetrically according to J. F. Inman and H. M. Dintzis, (1969) Biochemistry 8, 4074–4082) and stored at −20° C.

2. Bilayer encagement of glucose oxidase 2-(a) Into a 20 ml beaker equipped with a magnetic stirrer and thermostated at 4° C., 9.8 ml of 10 mg/ml solution of polymeric glutaraldehyde in 0.2M phosphate pH 8.2 were added, followed by 0.2 ml of 50 mg/ml glucose oxidase solution in 0.2M phosphate pH 6.0. The coupling reaction was allowed to proceed for 3 hrs at 4° C. The non-bound polymer was removed by dialysis (3 times against 0.2M phosphate buffer pH 8).

2-(b) Into a 20 ml beaker equipped with a magnetic stirrer and thermostated at 4° C., 16 ml of aminobutyl derivative of polyacrylamide solution (0.25 mg/ml in 0.2M phosphate, pH 8.0) were added, followed by 4 ml of polyglutaraldehyde coated glucose oxidase solution (obtained as described above). The reaction was allowed to proceed for 3 hrs at 4° C. and the pH adjusted to 6.0 by dialysis against 0.2M phosphate pH 6.0.

The stabilized enzyme was stored either as solution at 4° C. or as a lyophilized powder.

3. Stabilization of glucose oxidase to thermal inactivation:

The stabilization of glucose oxidase to thermal denaturation was demonstrated by measuring the rate of inactivation of the native or stabilized enzyme at a fixed elevated temperature (55° C.). The rate constant defined as:

$$K_{ina} = -\frac{\ln E(t)/E(o)}{t}$$

(for description of this method see ref. 24).

The data are presented in Table 1.

TABLE 1

Effect of bi-layer encagement on the thermal stability of glucose oxidase

| Enzyme | $K_{ina}$ ($h^{-1}$, 55° C.) | Relative $K_{ina}$ (%) | Residual activity after 5 h at 55° C. (%) |
|---|---|---|---|
| native (control) | 0.19 | 100 | 43 |
| polyglutaraldehyde-treated | 0.066 | 35 | 60 |
| bi-layer ("encaged") | 0.032 | 17 | 80 |

4. Stabilization of glucose oxidase to inactivation resulting from the presence of organic cosolvents The stabilization of glucose oxidase towards the denaturing effect of water miscible organic solvents was demonstrated by measuring the rate of inactivation ($K_{ina}$) for native and stabilized enzyme at a fixed elevated temperature (55° C.) in presence of 3.5M (20%) of cosolvent. The data are presented in Table 2.

TABLE 2

Effect of bi-layer encagement on the tolerance of glucose oxidase to organic solvents

| Co-solvent (all at 3.5 M) | Kina (h$^{-1}$ 55° C.) | | Relative b/a, % |
|---|---|---|---|
| | Native enzyme (a) | Encaged enzyme (b) | |
| none | 0.19 | 0.055 | 29 |
| ethyleneglycol | 0.16 | 0.074 | 46 |
| DMSO | 0.19 | 0.075 | 40 |
| DMF | 0.40 | 0.22 | 55 |
| ethanol | 1.020 | 0.40 | 39 |
| formamide | 1.74 | 0.50 | 29 |

EXAMPLE 2

Stabilization of Pig Liver Esterase (E.C.3.1.1.1.) by Bi-Layer Encagement.

1. Preparation of polymeric reagents

Polymeric polyglutaraldehyde and polyacrylamide were prepared as described in Example number 1.

An acylhydrazide-derivative of polyacrylamide was prepared as follows: Into a 100 ml round bottomed flask equipped with a magnetic stirrer and maintained at 50° C., 38 ml of water and 1.5 g of polyacrylamide were added. Following complete dissolution 12 ml (0.23 mole) hydrazine hydrate were added and the hydrazinolysis reaction allowed to proceed for 4 hrs. The acylhydrazide derivative thus obtained was separated by precipitation induced by the dropwise addition of the aqueous reaction solution into 250 ml of methanol, recovered by centrifugation, redissolved and reprecipitated as above, stored overnight at 4° C. under methanol, separated and dried on a rotavapour (30 min at 40° C.) and finally dessicated in vacuo over $P_2O_5$. The dry polymer (acyl-hydrazide content: 1.5 mmole/gm, determined according to ref. 19, yield: essentially quantitative) was stored at −20° C.

2. Bilayer encagement of pig-liver esterase 2-(a) Into a 50 ml beaker equipped with a magnetic stirrer and thermostated at 4° C., 19.7 ml of 4 mg/ml polyglutaraldehyde solution in 0.05M phosphate pH 8.0 were added followed by 0.3 ml of 11 mg/ml enzyme stock solution (Sigma, Cat. No. E-3128). The coupling reaction was allowed to proceed at 4° C. for 3 hrs and excess of polyglutaraldehyde was removed by dialysis (three times against 0.05M phosphate, pH 8.0).

2-(b) Into a 100 ml beaker, equipped with a magnetic stirrer and thermostated at 4° C., 41 ml of 5 mg/ml acylhydrazide derivative of polyacrylamide in 0.05M phosphate, pH 8, were added, followed by 19 ml of polyglutaraldehyde enzyme solution (obtained as described above). The reaction was allowed to proceed at 4° C. for 3 hrs and finally dialysed against 0.05M Tris buffer pH 8. The stabilized enzyme was stored as solution at 4° C. or as lyophilized powder.

3. Stabilization of pig liver esterase to thermal inactivation

The stabilization of pig liver esterase to thermal denaturation was demonstrated by measuring Kina (h$^{-1}$, 55° C.) as described in Example 1. The data are presented in Table 3.

TABLE 3

Effect of bilayer encagement on the thermal stability of pig liver esterase.

| Enzyme | Kina (h$^{-1}$, 55° C.) | Relative Kina (%) | Residual activity after 5 h at 55° C. (%) |
|---|---|---|---|
| native (control) | 0.140 | 100 | 47 |
| polyglutaraldehyde-treated | 0.047 | 34 | 50 |
| bi-layer ("encaged") | 0.032 | 23 | 82 |

4. Stabilization of pig liver esterase to the presence of water miscible solvents Stabilization to the denaturing effect of water miscible cosolvents present in 3.5M (≈20%) concentration was demonstrated as described in Example 1. The data are presented in Table 4 and they relate to lyophilized encaged enzyme preparations.

TABLE 4

Effect of bilayer encagement on the tolerance of pig liver esterase to organic solvents.

| Co-solvent (all at 3.5 M) | Kina (h$^{-1}$, 55° C.) | |
|---|---|---|
| | Native enzyme | Encaged enzyme (lyophilized) |
| none | 0.14 | 0.00 |
| ethyleneglycol | 0.24 | 0.00 |
| DMSO | 0.24 | 0.01 |
| propyleneglycol | 0.50 | 0.00 |
| ethanol | 2.95 | 0.093 |

EXAMPLE 3

Stabilization of β-Lactamase (E.C.3.5.2.6) Bilayer Encagement

1. Preparation of polymeric reagents: polyglutaraldeyde was prepared as described in Example 1. Polyacrylamide, partially substituted with acylhydrazide groups was prepared as described in Example 2.

2. The two stage procedure was carried out essentially as described in Example 2 for pig liver esterase.

3. Stabilization of β-lactamase to thermal denaturation by bilayer encagement according to the invention was demonstrated by measuring Kina (h$^{-1}$, 55° C.) as described in Example 1. The data are shown in Table 5.

TABLE 5

Effect of bi-layer encagement on the thermal stability of β-lactamase

| Enzyme | Kina (h$^{-1}$, 55° C.) | Relative Kina (%) | Residual activity after 5 h at 55° C. (%) |
|---|---|---|---|
| native (control) | 0.52 | 100 | 10 |
| polyglutaraldehyde | 0.10 | 19 | 28 |

TABLE 5-continued

Effect of bi-layer encagement on the thermal stability of β-lactamase

| Enzyme | Kina (h$^{-1}$, 55° C.) | Relative Kina (%) | Residual activity after 5 h at 55° C. (%) |
|---|---|---|---|
| treated bi-layer ("encaged") | 0.03 | 6 | 70 |

EXAMPLE 4

Stabilization of "Caged" Enzymes by Lyophilization

Lyophilization of "caged" enzymes resulted in significant further improvement of enzyme stability. This effect is in contrast to the common effect of lyophilization on native enzymes; in many cases their stability declines, in others it remains unchanged.

The effect of lyophilization on "caged" enzyme stability is demonstrated in Table 6 for pig liver esterase and β-lactamase.

TABLE 6

Effect of lyophilization on the thermal stability of "caged" and native enzymes

| | Kina (h$^{-1}$, 55° C.) | |
|---|---|---|
| Enzyme | Before lyophilization | Following lyophilization |
| Pig-liver esterase-native | 0.12 | 0.14 |
| Pig-liver esterase "caged" | 0.032 | 0.00 |
| β lactamase - native | 0.52 | 2.59 |
| β lactamase - "caged" | 0.03 | 0.00 |

EXAMPLE 5

Immobilization and Stabilization of Lyophilized "Caged" Enzyme

Immobilization Procedure

Into a 1.5 g solution of polyacrylhydrazide (MW 100,000) in 8.5 ml of distilled water, 0.5 ml of 1M phosphate buffer (pH 8) was added and thoroughly mixed. A buffered solution of a lyophilized "encaged" pig liver esterase prepared as in Example 2 (150 mg in 1 ml of 0.05M phosphate, pH 8, 30 EU) was then added, thoroughly mixed by magnetic stirring and the solution thus obtained injected (injector outlet 2 mm) into an ice-cold 1% glyoxal solution. The gel "noodles" thus obtained were allowed to harden for one hour and then fragmented into fragments of about 2 mm by pressing through a syringe (outlet diameter 2 mm). The gel was then incubated at 4° C. for 20 h and further fragmented into particles of about 0.25 mm by means of a blade homogenizer ("Sorval Omnimixer", 7000 rpm, 1 min). The gel particles were washed with 1 l of ice cold 0.05M Tris buffer (pH 8), resuspended in 50 ml of the same buffer and stored at 4° C. until used.

The thermal stability—at 55° C.—of this preparate is shown in FIG. 2.

We claim:

1. A stabilized, biologically active, water-soluble enzyme product, comprising
   enzyme molecules having a bi-layer protective structure comprising
   a polyaldehyde base coat linked to free amino groups of the enzyme, and cross-linked therewith an outer polymer coat,
   the polymer constituting said outer coat being of a kind which in the unlinked state comprises at least one of free amino and acyl hydrazide groups.

2. A method of making a stabilized, biologically active enzyme product according to claim 1, wherein
   in a first step, a native enzyme product is reacted in aqueous solution with an excess of a water-soluble polyaldehyde to produce an intermediary enzyme product in which the enzyme molecules are coated with said polyaldehyde base coat, and
   in a second step, said intermediary enzyme product is reacted in aqueous solution with a polymeric reagent bearing at least one of free amino and free acyl hydrazide groups.

3. A method according to claim 2, wherein the product obtained in said second step is lyophilized.

4. An enzyme product according to claim 1, being immobilized within a matrix.

5. A method of making an enzyme product, wherein an aqueous solution obtained at the end of said second step as defined in claim 2 and which contains unreacted polymer, is subjected to a cross-linking reaction, whereby said enzyme product is immobilized within a matrix.

6. An enzyme product according to claim 1, being in form of an aqueous solution.

7. An enzyme product according to claim 1, being a lyophilized dry product.

8. An enzyme product according to claim 1, wherein said base coat is made of polyglutaraldehyde.

9. An enzyme product according to claim 1, wherein said outer coat is made of a polymer selected from the group of polyacrylamides, N-alkylated polyacrylamides and acylhydrazide derivatives of polyacrylamides.

10. An enzyme product according to claim 1, wherein the enzyme is glucose oxidase.

11. An enzyme product according to claim 1, wherein the enzyme is pig liver esterase.

12. An enzyme product according to claim 1, wherein the enzyme is β-lactamase.

13. The enzyme product of claim 1, wherein said outer coat is made of a polymer selected from polyacrylamides, N-alkylated polyacrylamides, acyl hydrazide or amino derivatives of polyacrylamides, polyvinyl hydrazines, polyvinylamines, and polylysine.

14. The enzyme product of claim 1, wherein said outer coat is made of polyacrylamide-amine or acyl hydrazide derivatives.

15. The enzyme product of claim 1, wherein said enzyme is carboxylesterase.

16. The enzyme product of claim 1, wherein each molecule is encaged within a protective bilayer.

* * * * *